Figure 1:
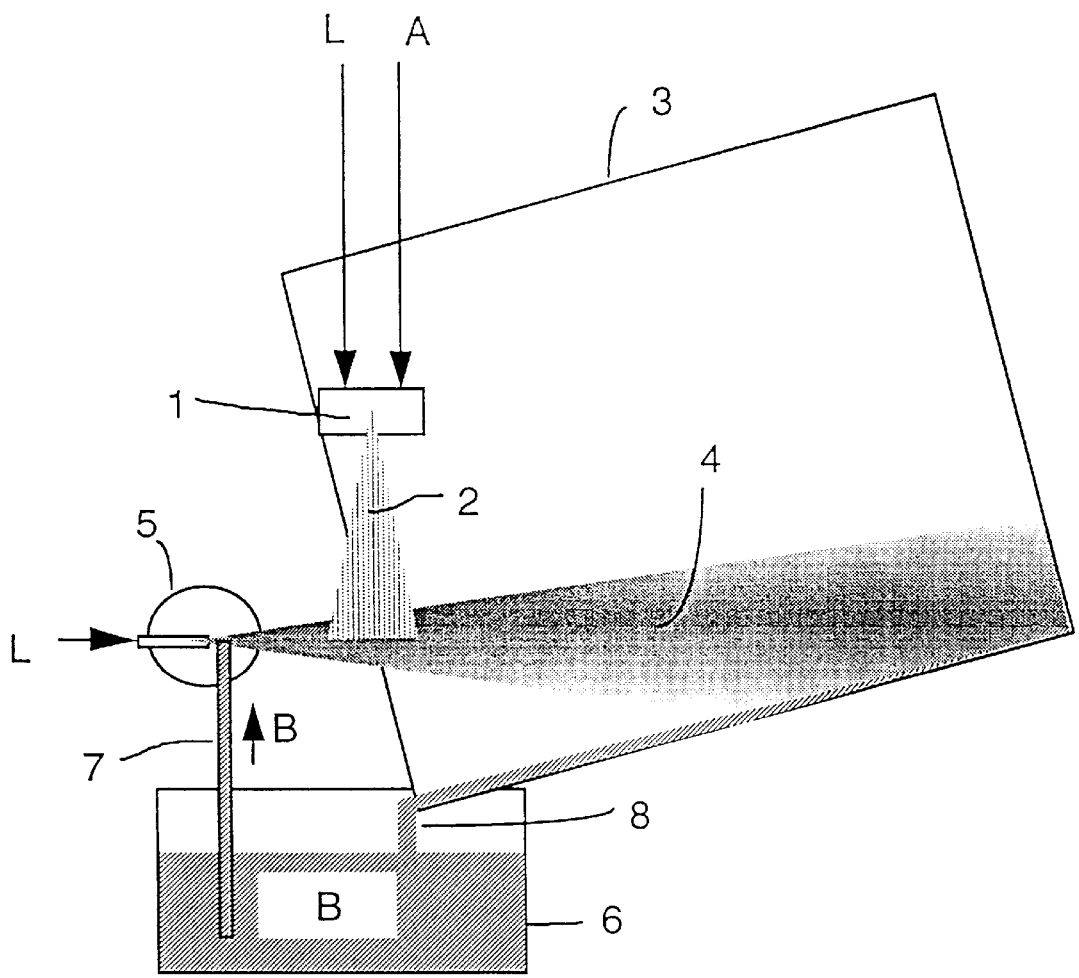
Figure 2:
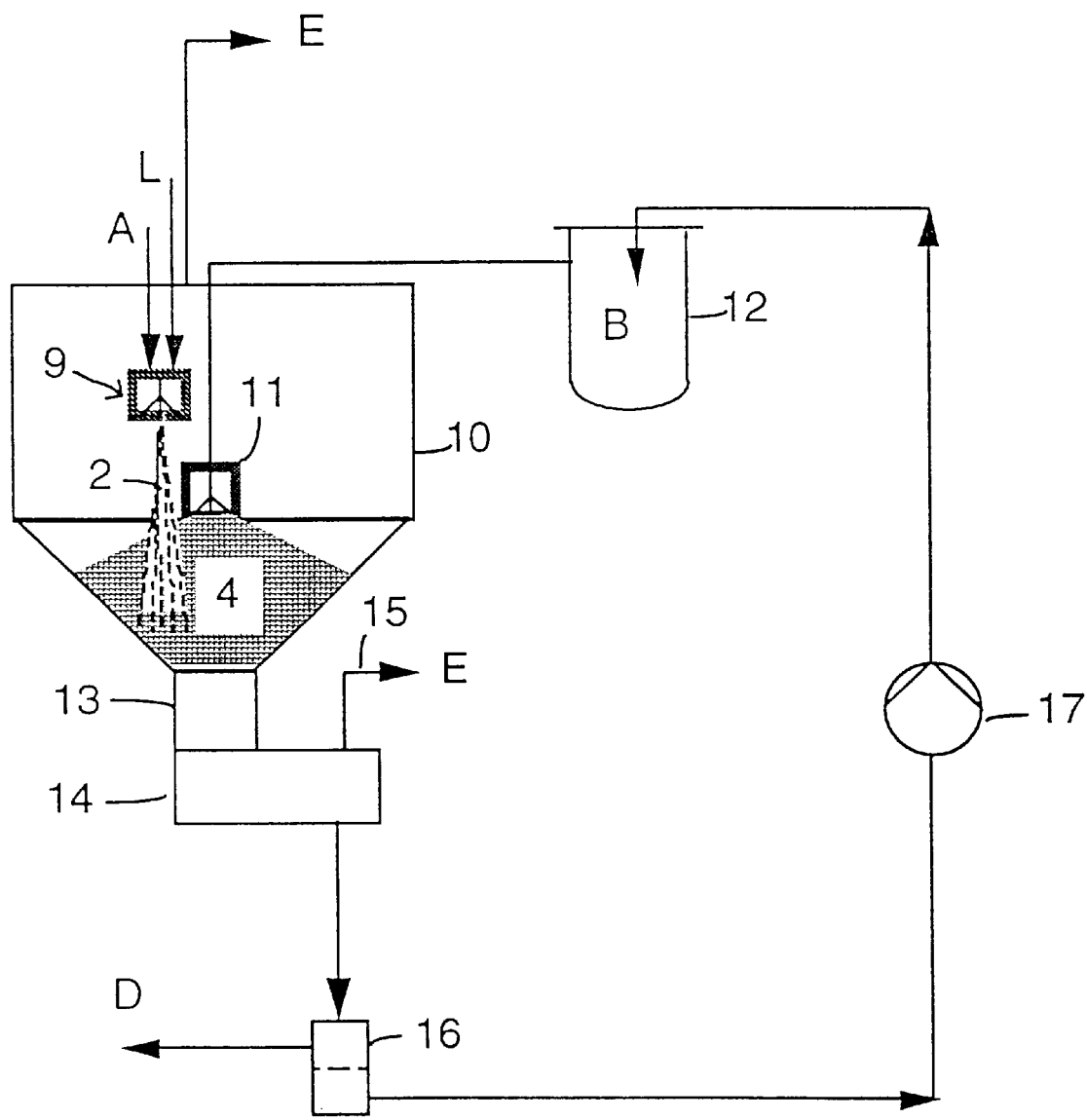

United States Patent [19]
Schulte et al.

[11] Patent Number: 6,074,441
[45] Date of Patent: Jun. 13, 2000

[54] PROCESS FOR PRODUCING ULTRAFINE-CRYSTALLIZATION PRODUCTS

[75] Inventors: Barbara Schulte, Bomlitz; Stefan Hofmann, Langenfeld; Andre Fellhölter, Köln; Heiko Herold, Neuss; Frank Behrendt, Hitdorf, all of Germany

[73] Assignee: Bayer Aktiengesellschaft, Leverkusen, Germany

[21] Appl. No.: 08/848,005

[22] Filed: Apr. 28, 1997

[30] Foreign Application Priority Data

Apr. 29, 1996 [DE] Germany ............... 196 17 085

[51] Int. Cl.$^7$ ............... B01J 25/00; B01D 9/02; C07C 7/14
[52] U.S. Cl. ............... 23/300; 23/295 R; 23/293 P; 585/812; 585/816
[58] Field of Search ............... 23/313 R, 293 A, 23/300; 585/812, 816

[56] References Cited

U.S. PATENT DOCUMENTS

| | | |
|---|---|---|
| 2,728,678 | 12/1955 | Sharp . |
| 3,929,291 | 12/1975 | Ladisch ............... 239/425 |
| 4,031,301 | 6/1977 | Vinansky, Jr. et al. . |
| 4,064,063 | 12/1977 | Alder et al. . |
| 4,275,048 | 6/1981 | Stein et al. ............... 423/329 |
| 4,985,239 | 1/1991 | Yahagi et al. . |
| 5,043,280 | 8/1991 | Fischer et al. . |
| 5,496,564 | 3/1996 | Asakura et al. . |
| 5,637,560 | 6/1997 | Raehse et al. ............... 510/443 |

FOREIGN PATENT DOCUMENTS

| | | |
|---|---|---|
| 927405 | 5/1973 | Canada . |
| 1267666 | 5/1968 | Germany . |
| 1924152 | 11/1969 | Germany . |
| 3744329 | 7/1989 | Germany . |
| 03833446 | 4/1990 | Germany . |
| 3835728 | 4/1990 | Germany . |
| 4118185 | 12/1992 | Germany . |
| 4425968 | 2/1996 | Germany . |
| 1118908 | 7/1968 | United Kingdom . |
| 8102688 | 10/1981 | WIPO . |
| 9407582 | 4/1994 | WIPO . |

OTHER PUBLICATIONS

E. Nürnberg, et al., Hagers Handbuch der pharmazeutischen Praxis, Springer–Verlag, Berlin, Heidelberg, New York, Bd. 2, pp. 549 and 929, (1991).

Sugimoto, Tadao. "Preparation of monodispersed colloidal particles", Advances in Colloid and Interface Science 28 (1987) pp. 65 –108.

Matijevic, Egon "The world of fine particles (ultrafine particles produced by precipitation or chemical reactions with drops)", Chemtech 21 (Mar. 1991), pp. 176–181.

Sjöström Brita; Kronberg, Bengt; Carlfors, Johan ."A Method for the Preparation of Submicron particles of Sparingly Water–Soluble Drugs by Precipitation in Oil–in–Water Emulsions: part I & part II", Pharm. Sci 82 (6), (1993), pp. 579–589.

Horn, Dieter "Preparation and Characterization of Microdisperse Bioavailable Carotenoid Hdrosols",. Die angewandte makromolekulare Chemie 166/167 (1989), pp. 139–153 (2874).

Bornschein, M.; Melegari, P.; Bismarck, C.; Keipert, S. "Mikro–und Nanopartikeln als Arzneistoffträgersysteme unter besonderer Berücksichtigung der Herstellungsmethoden (The use of micro–and nanoparticles as drug vehicle systems giving special consideration to the production methods)", s. Die Pharmazie 44(9) (1989) pp. 585–593.

Primary Examiner—Gary P. Straub
Attorney, Agent, or Firm—Norris McLaughlin & Marcus

[57] ABSTRACT

The process for producing crystallisation products with an average particle diameter of <1 μm is based on the atomisation of a solution and the simultaneous evaporation of the solvent. The atomised solution A crystallises in a gas atmosphere, in which it is simultaneously contacted with a cloud of drops 4 of a surfactant-containing liquid B, thus forming an aerosol mixture A, B which is then deposited in the form of a colloidal crystal suspension in which the surfactant-containing liquid B forms the continuous phase. The cloud of drops 4 of the surfactant-containing liquid can also be produced by atomisation.

9 Claims, 3 Drawing Sheets

PROCESS FOR PRODUCING ULTRAFINE-CRYSTALLIZATION PRODUCTS

Process for producing ultrafine crystallisation products The invention relates to a process for producing crystallization products with an average particle diameter of <1 µm by atomizing a solution and simultaneously evaporating the solvent. In this process crystals are formed by atomizing the product solution and evaporating the solvent.

Nanoparticles can be produced by many different methods, of which overviews are provided for example in "Preparation of monodispersed colloidal particles" (Sugimoto, T., Advances in colloid and interface science 28 (1987) pp. 65–108) and "The world of fine particles (ultrafine particles produced by precipitation or chemical reactions with drops)" Matijevic, E., (Chemtech 21 (1991) 3, pp. 176–181).

The methods described in the above references are however used almost exclusively for the production of inorganic particles. They include for example precipitation processes in surfactant systems or microemulsions for the production of oxides "Verfahren zur Herstellung nanoskaliger Oxidteilchen (Process for the production of nanoscale oxide particles)", Schmidt, H., DE 4 118 185 A1, Jun. 3, 1991 or noble metals "Suspension of platinum group metal particles in microemulsion with uniform particle size, useful for making catalysts", Stenius, P., WO 81/02688, Oct. 1, 1981.

Some literature references are also concerned with methods for the production of submicron particles of organic substances, and in particular pharmaceutically active compounds.

In "A method for the preparation of submicron particles of sparingly water-soluble drugs by precipitation in oil-in-water emulsions: part I & part II", Sjöström Brita, Kronberg B., Carifors J. J. Pharm. Sci 82 (6), (1993), pp. 579–589, there is described the preparation of sparingly water-soluble active compounds from oil-in-water emulsions. The fine solids are formed from the drops of oil containing the dissolved substance by evaporating off the oil in a rotary evaporator. The concentration of the solid substance (cholesteryl acetate) is approximately 1–2% by weight where particles smaller than 1 micrometer are produced and the content of surfactant in relation to the organic phase is stated to be up to 20% by weight. In experiments carried out by the applicants it was discovered that this method of procedure is only effective for specific product systems since it was not possible to obtain stable colloidal suspensions using two other test substances (including naphthalene).

According to "Preparation and characterization of microdisperse bioavailable carotenoid Hydrosols", D. Horn. Die angewandte makromolekulare Chemie 166/167 (1989), pp. 139–153 (2874), a bioavailable carotenoid hydrosol is obtained by dissolving the carotenoid in a water-miscible solvent at a high temperature (>100° C.) followed by rapid precipitation in water in the presence of a stablilizing polymer colloid. No details of the solids content or the content of surfactant are provided. The size of the particles is between 50 nm and 500 nm.

"Mikro- und Nanopartikeln als Arzneistoffträgersysteme unter besonderer Berücksichtigung der Herstellungsmethoden (The use of micro- and nanoparticles as drug vehicle systems giving special consideration to the production methods)", Bornschein M., Melegari P., Bismarck Ch., Keipert, s. Die Pharmazie 44(9) (1989) pp. 585–593 contains an overview on the use of micro- and nanoparticles as drug vehicle systems, although the atomization methods mentioned superficially in this reference do not provide any concrete example of how to produce nanoparticles.

The invention is based on the problem of producing a crystal suspension of inorganic and in particular organic compounds, the particle sizes of which are narrowly distributed to monodisperse and whose average particle diameter is less than 1 micrometer. This particle size must remain stable for at least a period of several days to 2 weeks.

The exposure of the compound to be crystallized to high temperatures must be avoided. It must also be possible to adjust the solids contents of the suspension to values of higher than 1% by weight.

The above problem is solved by a process in which a solution is atomized and the solvent evaporated. According to the invention the atomized solution A is crystallized in a gas atmosphere and simultaneously brought into contact with a cloud of drops of a surfactant-containing liquid B, thus forming an aerosol mixture A/B which is then deposited in the form of a colloidal crystal suspension, in which the surfactant-containing liquid forms the continuous phase.

Preferably the cloud of drops of surfactant-containing liquid B is also produced by atomization.

The process is either conducted in such a manner that the solution A is injected into the cloud of drops of surfactant-containing liquid B or—vice versa—the surfactant-containing liquid B is injected into the atomized solution A.

Advantageously the crystal suspension is at least partially recycled and atomized in the form of surfactant-containing liquid B.

One variant advantageously used in a continuously operated process comprises concentrating the crystal suspension in a separating apparatus, recycling the depleted crystal suspension and atomizing it in the form of surfactant-containing liquid B.

In order to intensify the mixing of the cloud of drops with the atomized solution A, the aerosol mixture A/B formed can be passed through a gas scrubber.

The solvents preferably used for the compound to be crystallized are readily volatile liquids which have a vapor pressure of >0.1 mbar at room temperature.

Water containing a surfactant as an additive is appropriately used as the surfactant-containing liquid.

An additional option comprises also adding a surfactant to solution A.

One important use of the process is the employment of the crystal suspension as a formulation for parenteral drug preparations.

The production of particles of a size range of smaller than 1 micrometer is highly important for industrial uses, since the property profile of the colloidal particles is considerably different from that of conventional particles of a size above the 1-micrometer threshold. As far as organic particles are concerned, and in particular pharmaceutically active compounds, these properties include for example a change in their dissolving power ("bioavailability") or their capacity to be used in the form of a parenteral solution for pharmaceutical purposes despite their particulate nature ("depot effect").

The obtainment of nanoparticles by the direct production of native crystals has considerable advantages over their production by means of mechanical comminution (such as for example bead-milling). In the comminution process fracture surfaces are formed which, from an energetic point of view, have an increased tendency to heal and grow, as a result of which the size of the particles increases once again as a result of recrystallization or agglomeration.

The present process is particularly suitable for the production of organic crystals, whereas most of the other processes for the production of nanoparticles are only suitable for the production of inorganic ultrafine particles, due to the process parameters employed (e.g. high temperatures).

The abovementioned method of surfactant-stabilized spray crystallization also has the advantage that it is not necessary to produce a preliminary emulsion of the substance to be crystallized.

By contrast, the solution of the required solid which is instead used can be of any desired concentration, depending on the solubility of the solid concerned, and, provided that a suitable solvent is used, a very high content of product can be obtained.

The dispersing and homogenizing energy necessary (for example using Ultra-Turax or high pressure homogenization) for the production of emulsions is dispensed with. Also, there is no need for a possibly critical search for surfactant combinations for stabilizing the product system to be emulsified.

A simple, non-pulsating pump system (such as for example a spray pump) can be used for processing the solution. High pressures (>10 bars) or high temperatures (>100° C.) are not required. This makes the method particularly suitable for temperature-sensitive organic substances.

By atomizing the solution into fine drops the vapor pressure of the solvent is increased, so that ambient pressure or a slight vacuum is sufficient for removing the solvent. This is an advantage compared with methods in which the solvent has to be removed from the complete emulsion under a high vacuum.

The particles are formed from the evaporating droplets of the atomized solution and, in the method of procedure used according to the invention, are intercepted by surfactant-containing drops of water while they are still in the process of drying. The commercially available surfactants which are suitably selected (such as for example from the point of view of their high wetting and stabilizing capacity for boundary surfaces) surround the crystallite formed and thus substantially prevent any further mass transfer processes. Processes of agglomeration and recrystallization of the colloidal particles can therefore be prevented. The quantity of recycled surfactant-containing water used can be adjusted as desired according to the required concentration of solids in the product suspension. If required, a concentrated partial stream containing the finished nanoparticles can be drawn off by means of a prefiltration step incorporated in the circuit.

The method of procedure employed can be used both for continuous and batchwise types of operation.

In the following the invention is described in more detail by way of practical examples and drawings.

FIG. 1 illustrates the principle of an experimental unit

FIG. 2 is a diagram of an industrial unit and

FIG. 3 is an electron-microscopic photograph of the crystallites formed.

The particular substance A to be crystallized is dissolved in a readily volatile solvent. As shown in FIG. 1 this solution A is conveyed through the 0.4 mm duct of a two-component nozzle 1, whereas the compressed air L at an absolute pressure of for example 3 bars required for the operation of the two-component nozzle passes through 6 boreholes leading to the narrowest cross-section of the concentric aperture of the two-component nozzle having an equivalent diameter of 0.55 mm. As a result ultrafine droplets (aerosol) in the form of a spray cone 2 are produced in chamber 3. While the solvent evaporates, the dissolved substance crystallizes in an ultrafine form. Before the spray cone 2 can impinge upon the wall surfaces of the surrounding spraying chamber 3 it is penetrated by a cloud of drops 4 injected into the chamber and consisting of a stabilizing phase. The stabilizing phase used is for example water to which 10% by weight of a surfactant has been added.

The cloud of drops 4 is produced with the aid of an atomizing device 5. In this manner the freshly produced nano-sized crystal particles are wetted with surfactants. According to FIG. 1, in order to atomize the surfactant-containing water contained in reservoir 6, a simple glass atomizer, which, just as the two-component nozzle 1, is filled with compressed air L, can be used for atomizing the surfactant/water mixture supplied via ascending pipe 7.

The aerosol mixture A/B produced in chamber 3 as a result of the penetration of the spray cone 2 by the cloud of drops 4 is deposited on the walls of chamber 3 and forms the required colloidal crystal suspension which flows freely downwards from chamber 3 into reservoir 6 in the form of a liquid layer 8. At the beginning of the process only the surfactant-containing water had been present in container 6. Since fresh solution is continuously introduced through the two-component nozzle 1 during the process the concentration of solids in container 6 constantly increases. The process is terminated as soon as the crystal suspension in container 6 has reached the required final concentration.

An important step during crystallization is the removal of the solvent. For this reason its evaporation from the product-containing solution A must be as spontaneous as possible.

One industrial setup for carrying out the process according to the invention is illustrated in FIG. 2.

The product-containing liquid A is atomized with compressed air L through a miniature two-component nozzle 9 to form a spray cone 2 in a closed chamber 10. In this process, ultrafine crystallites are formed, as already described in relation to FIG. 1, due to the spontaneously occurring evaporation of the solvent. Before this spray cone can impinge upon the wall surfaces of the surrounding chamber 10, it penetrates a cloud of drops 4, consisting of surfactant-containing drops of water, which wets the crystallites and is formed with the aid of a commercially available one-component or two-component nozzle 11. The mininozzle 9 is filled with surfactant-containing water B which is present in container 12. Immediately downstream of the exit to chamber 10, a Venturi scrubber 13 is arranged in which the surfactant-containing drops of water are brought into intense contact with the product/air aerosol jet (spray cone 2) issuing from the miniature two-component nozzle 9. The resulting aerosol of drops containing the crystals flows from the Venturi scrubber into a gas separator 14. The off-gas E formed from the stream of air L used for atomization and the evaporating portions of solvent from solution A is partly discharged directly from the spraying chamber 10 and partly discharged through pipe 15 as the aerosol accumulates in separator 14 and is delivered for reprocessing or disposal. In order to remove the solvent vapors more effectively, chamber 10 can also be operated under a slight vacuum.

The crystal suspension in separator 14 contains the nanometer-sized product crystals which are concentrated further in an additional step by means of a crossflow filter 16 and discharged in the form of a suspension D with a higher content of solids, whereas the surfactant-containing filtrate is recycled into container 12 by means of pump 17.

EXPERIMENTAL EXAMPLE

In the apparatus according to FIG. 1 the process according to the invention was carried out on a laboratory scale using the following data:

a) The temperature was approx. 20° C. (room temperature).

b) The solution A consisted of a 5% by weight naphthalene/chloroform solution with a density of 1.5 g/ml (0.75 g of naphthalene in chloroform, altogether 15 g). At room temperature chloroform has a vapor pressure of 0.211 mbar and a water-solubility of 0.82% by weight.

c) The surfactant-containing liquid B consisted of 3.17 g of Triton®×100 (a non-ionic surfactant), 1.93 g of Marlon® A 375 (anionic: Nadodecylbenzene sulphonate) and 44.9 g of water (surfactant content approx. 10% by weight). This surfactant mixture has a high wetting and stabilizing capacity for boundary surfaces. The abovementioned surfactants are inexpensive industrial commercial products.

d) A spray pump was used for the metered introduction of solution A. The volumetric flow of solution A was 60 ml/h during the 15 minute test duration.

e) The compressed air L was introduced at an absolute pressure of 3 bars, which corresponds to a throughput of approx. 500 l/h of air in the two-component nozzle 1.

Figure 3:
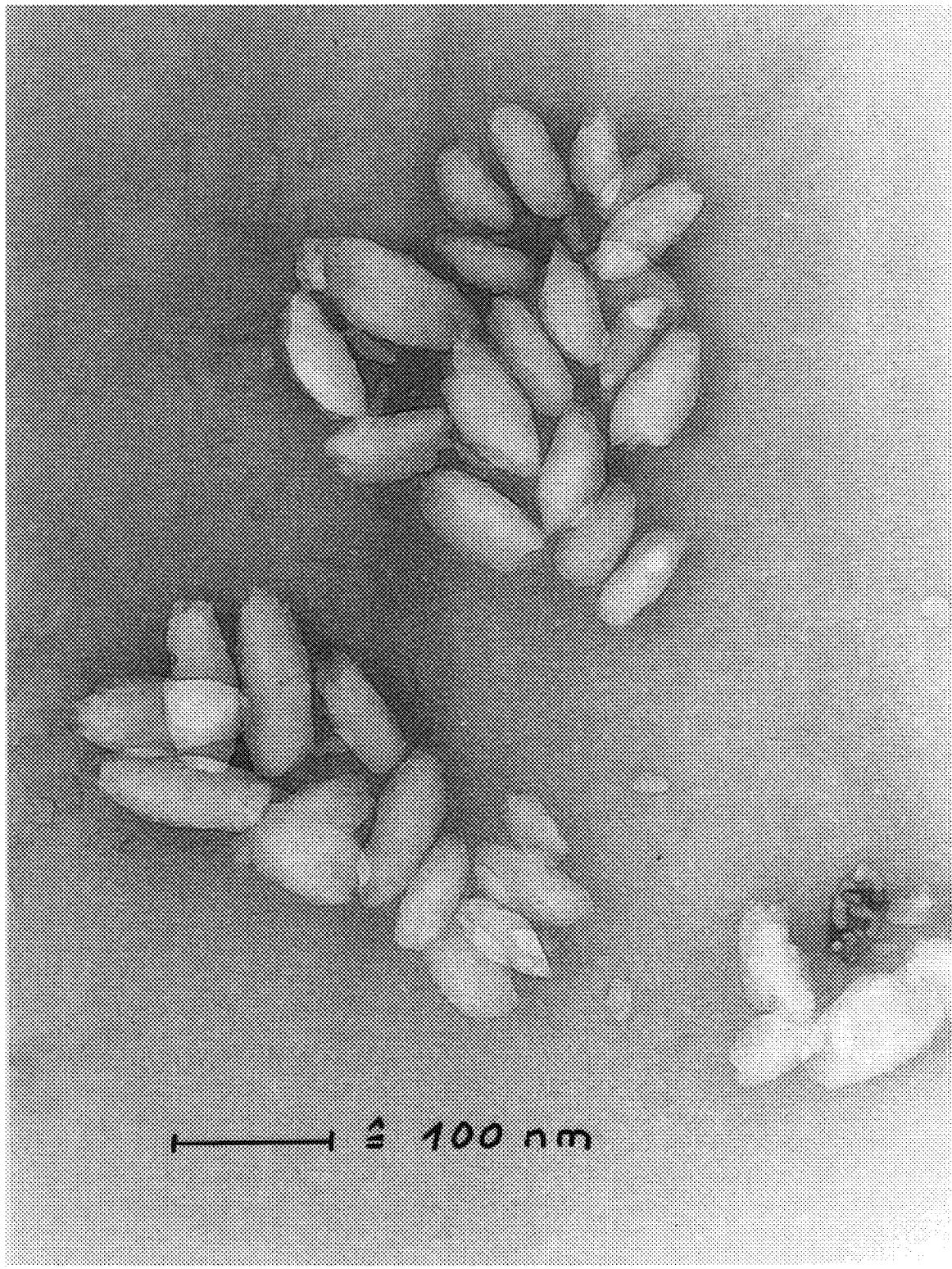

Samples of the crystal suspension thus produced were examined by electron microscopy (TEM photograph, see FIG. 3) for their final particle size distribution. In the photograph the almost ellipsoid crystallites are easily recognizable. In the photograph, 8 mm correspond to 1 micrometer of the sample. The particles have a size in the range of 100 nm and a narrow particle size distribution. No recrystallized particles could be detected even after a retention time of 19 days. Mathematically (without taking losses into account) the solids concentration was 1.5% by weight and the surfactant concentration 10% by weight in the colloidal crystal suspension.

We claim:

1. Process for producing crystallization products having an average particle diameter of <1 $\mu$m by atomizing a solution of a water insoluble solid material in a solvent and simultaneously evaporating the solvent, to produce crystallite particles of said solid, simultaneously bringing said particles into contact with a cloud of drops (4) of a surfactant-containing water, thus forming an aerosol mixture of said particles and said surfactant-containing water, which is then deposited in the form of a colloidal crystal suspension in which the surfactant-containing water forms the continuous phase.

2. Process according to claim 1, wherein the cloud of drops (4) of the surfactant-containing water is also produced by atomization.

3. Process according to claim 2, wherein said solution of said solid material is injected into the cloud of drops (4) of the surfactant-containing water or the surfactant-containing water is injected into the atomized solution.

4. Process according to claim 1, wherein the crystal suspension is at least partially recycled and atomized in the form of a surfactant-containing water.

5. Process according to claim 1, wherein the crystal suspension is concentrated in a separating apparatus (16) and the depleted crystal suspension is recycled and atomized in the form of a surfacant-containing water.

6. Process according to claim 1, wherein the aerosol mixture is passed through a gas scrubber (13) in order to intensify the mixing process.

7. Process according to claim 1, wherein the solvent for the solid material to be crystallized has a vapor pressure of >0.1 mbar at room temperature.

8. Proces acordng to claim 1, wherein a surfactant is also added to said solution of said solid material.

9. The process of claim 1, wherein said solution is a solution of naphthalene in chloroform.

* * * * *